(12) United States Patent
Mastenbroek et al.

(10) Patent No.: US 7,759,873 B2
(45) Date of Patent: Jul. 20, 2010

(54) ELECTRONIC LAMP IDENTIFICATION SYSTEM

(75) Inventors: Olaf Mastenbroek, Turnhout (BE); Klaas Jacob Lulofs, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 248 days.

(21) Appl. No.: 11/912,315

(22) PCT Filed: Apr. 20, 2006

(86) PCT No.: PCT/IB2006/051217

§ 371 (c)(1), (2), (4) Date: Oct. 23, 2007

(87) PCT Pub. No.: WO2006/114730

PCT Pub. Date: Nov. 2, 2006

(65) Prior Publication Data

US 2008/0185539 A1 Aug. 7, 2008

(30) Foreign Application Priority Data

Apr. 26, 2005 (EP) .................... 05103374

(51) Int. Cl.
*G01J 1/00* (2006.01)
(52) U.S. Cl. .................... 315/34; 250/493.1; 250/505.1; 340/635; 340/657; 324/403; 324/410; 315/32

(58) Field of Classification Search .............. 250/493.1, 250/503.1, 504 R, 505.1; 340/500, 540, 340/635, 654, 657; 324/403, 410; 702/34; 355/355; 315/32, 34; 343/701
See application file for complete search history.

(56) References Cited

U.S. PATENT DOCUMENTS

| 5,274,611 | A | 12/1993 | Donohoe |
| 5,493,183 | A | 2/1996 | Kimball |

(Continued)

FOREIGN PATENT DOCUMENTS

| CA | 2403463 A1 | 10/2001 |
| EP | 0813991 A1 | 12/1997 |

(Continued)

*Primary Examiner*—Bernard E Souw
*Assistant Examiner*—Michael J Logie

(57) ABSTRACT

An identification system for a light radiation source (103) having a control circuit (107) for communicating with an identification circuit (108) associated with the light radiation source, wherein the identification circuit is arranged for storing data relating to the light radiation source. During operation, the control circuit communicates with the identification circuit via a signal path comprising at least a portion of a first electric wire (112) provided for energizing the light radiation source such that it is used as a first transmitting antenna for communicating with the identification circuit. The operation of the light radiation source is controlled in dependence on the data retrieved from the identification circuit. Depending on the result of the identification, operation of the light radiation source can be authorized or prevented, thus blocking the use of an incorrect radiation source for a given application.

20 Claims, 6 Drawing Sheets

U.S. PATENT DOCUMENTS

| | | | |
|---|---|---|---|
| 6,268,799 B1* | 7/2001 | Miyashita et al. | 340/641 |
| 6,436,299 B1* | 8/2002 | Baarman et al. | 210/748 |
| 6,809,652 B1* | 10/2004 | Baxter et al. | 340/815.4 |
| 6,894,616 B1* | 5/2005 | Forster | 340/572.1 |
| 7,154,378 B1* | 12/2006 | Ertas et al. | 340/5.85 |
| 7,225,992 B2* | 6/2007 | Forster | 235/492 |
| 7,382,270 B2* | 6/2008 | Wendelrup et al. | 340/636.1 |
| 2001/0005172 A1* | 6/2001 | Miyashita et al. | 340/641 |
| 2002/0189986 A1* | 12/2002 | Kuennen et al. | 210/109 |
| 2003/0060682 A1* | 3/2003 | Handa et al. | 600/178 |
| 2004/0080715 A1* | 4/2004 | Miyashita et al. | 353/30 |
| 2004/0113102 A1* | 6/2004 | Wedekamp | 250/504 |
| 2005/0105140 A1* | 5/2005 | Ozaki | 358/402 |

FOREIGN PATENT DOCUMENTS

| | | |
|---|---|---|
| EP | 0833548 A1 | 4/1998 |
| WO | 0078678 A2 | 12/2000 |

* cited by examiner

ELECTRONIC LAMP IDENTIFICATION SYSTEM

TECHNICAL FIELD

The invention relates to an identification system for a light radiation source, comprising a control circuit for communicating with an identification circuit associated with the light radiation source, wherein the identification circuit is arranged for storing data relating to the light radiation source, and wherein, during operation, the control circuit communicates with the identification circuit via a signal path comprising at least a portion of a first electric wire provided for energizing the light radiation source.

The invention further relates to a method of operating a light radiation source, in which said identification system is used.

The invention further relates to a light radiation source suitable for cooperating with said identification system.

The invention further relates to a solarium comprising said identification system.

The invention further relates to a UV disinfection system comprising said identification system.

BACKGROUND ART

The dimensions and electrical contacts of a light radiation source, e.g. a lamp for general illumination purposes or for special lighting purposes, are often standardized. The term "light" refers to any magnetic radiation having a wavelength between 250 and 900 nm. However, the wattage, spectral distribution, and degree of efficiency in producing light radiation may be different for identical looking lamps, and hence the radiation intensity is different as well. In case of replacement of a lamp that has become unusable, the operation of a system for general illumination or for special lighting purposes is negatively affected if a lamp with either too high or too low a radiation intensity is installed. For example, a timer is often set in order to choose the degree of tanning in the case of a solarium. When the lamps of a solarium are replaced, installing lamps with a too high UV radiation output would cause sunburn of the user's skin. UV lamps used for disinfection purposes with a too low UV radiation output will result in an insufficient degree of disinfection. When using UV or infrared lamps, for example for medical purposes, a too low or too high luminous intensity of the lamps after incorrect lamp replacement may result in an improper treatment of the patient. An incorrect replacement of lamps for general illumination purposes may result in an insufficient level of illumination on the one hand or a too high power consumption and possibly damage to the lampholder on the other hand.

In mercury vapor discharge lamps, mercury constitutes the primary component for the generation of ultraviolet (UV) light. A luminescent layer comprising a luminescent material may be present on an inner wall of the discharge vessel to convert UV to other wavelengths, for example to UV-B and UV-A for tanning purposes (sun panel lamps) or to visible radiation for general illumination purposes or for the illumination of display devices. Such discharge lamps are therefore also referred to as fluorescent lamps. The discharge vessel of a low-pressure mercury vapor discharge lamp is usually circular and comprises both elongate and compact embodiments. Generally, the tubular discharge vessel of a compact fluorescent lamp comprises a collection of relatively short straight parts having a relatively small diameter; the straight parts being connected together by means of so-called bridge parts or via bent parts. Generally, means for maintaining a discharge in the discharge space are electrodes arranged in the discharge space.

The Canadian patent application CA 2 403 463 A1 describes a method and a device for operating a UV-radiation source. A UV-radiation source is disclosed, having an identification element that can be interrogated electrically and that is connected to the electrical connections of the radiation source, in parallel to the heating coil. Before a start of operation of the UV-radiation source, the UV lamp is identified by the identification element and, if the result of the identification is negative, operation of the lamp is prevented. Operation of the UV-radiation source is thus prevented if a mistake was made during lamp replacement.

It is a disadvantage of the prior art identification system that a proper functioning of the identification system is prohibited if the impedance of the lamp electrode is relatively low, for example with high signal frequencies in the range of 3-30 MHz, since the identification element cannot be interrogated reliably any more.

DISCLOSURE OF INVENTION

It is an object of the invention to provide an identification system for lamps that does not require a substantial modification of the power-supply circuit for energizing the lamp. This object is achieved with an identification system according to the invention, characterized in that the at least portion of the first electric wire is used during operation as a first transmitting antenna for communicating with the identification circuit. The control circuit and the identification circuit communicate via an existing electric wire and the existing electrical contacts provided for energizing the lamp. With the electric wire acting as an antenna, there is no need to modify the current-supply wiring or the electrical contacts. Furthermore, identification of the light radiation source is still possible in cases in which an electrode of the light radiation source has a relatively low impedance. In addition, identification of the lamp is even possible in the case of a relatively long electric wire having a relatively high inductance compared with a short electric wire, which is the case, for example, when electromagnetic ballasts are used for energizing a discharge lamp.

An embodiment of the identification system according to the invention is characterized in that the identification system is further arranged for controlling the operation of the light radiation source in dependence on data retrieved from the identification circuit. Only if the result of the identification is positive, the lamp is switched on, thus preventing an improper operation of a lighting device, for example after incorrect lamp replacement.

An embodiment of the identification system is characterized in that the identification system is further arranged to store information on or corresponding to the number of operating hours of the light radiation source. As the efficiency of a lamp decreases with an increasing number of operating hours, this information can be used to identify lamps that have to be replaced.

An embodiment of the identification system according to the invention is characterized in that the identification system is further arranged to generate a signal to alter the energizing of the light radiation source in dependence on the number of operating hours in order to maintain a substantially constant radiation output. If the decrease in efficiency of a lamp as a function of the number of operation hours is known, the supply of energy can be adapted in dependence on the number of operating hours in order to maintain a substantially constant light output.

An embodiment of the identification system according to the invention is characterized in that the identification system is further arranged to store information on or corresponding to the number of start-ups of the light radiation source. As the lifetime of a lamp is dependent on the number of start-ups, lamps that are near the end of their lifetime can be identified and replaced.

An embodiment of the identification system according to the invention is characterized in that the control circuit is arranged to communicate with the identification circuit by means of a modulated antenna current signal.

An embodiment of the identification system according to the invention is characterized in that the control circuit is coupled to a conducting ground, which provides a relatively simple manner of creating an antenna current signal, during operation of the system.

An embodiment of the identification system according to the invention is characterized in that the control circuit is coupled to the first electric wire and that the control circuit is coupled to a second electric wire provided for energizing the light radiation source, such that the second electric wire acts as a second transmitting antenna cooperating with the first transmitting antenna. If no conducting ground is available that can be used to provide a reference potential, this dipole antenna arrangement provides an alternative in using the first electric wire as an antenna for reading the identification circuit.

An embodiment of the identification system according to the invention is characterized in that the control circuit is arranged to communicate with the identification circuit by means of a modulated antenna voltage signal.

An embodiment of the identification system according to the invention is characterized by an electromagnetic ballast for energizing the light radiation source via the first electric wire, and a signal-passing device coupled to the first electric wire in parallel to the electromagnetic ballast for passing a signal used for communication between the control circuit and the identification circuit. This embodiment allows the use of an electromagnetic ballast for energizing the light radiation source.

An embodiment of the identification system according to the invention is characterized by a signal-blocking device, coupled in series with the electromagnetic ballast, for preventing the signal used for communicating with the identification circuit from proceeding in the direction of a power supply for energizing the electromagnetic ballast. This prevents the antenna signal from being coupled to the outside world.

According to the invention, a method of operating a light radiation source using an identification system according to claim 1 comprises the following steps: reading-out of data stored in the identification circuit; comparison of the read-out data with reference data; and authorization, prevention, interruption, or alteration of the operation of the light radiation source. If, for example, an incorrect lamp is installed, or the lamp has already been used for a given period of time, this method renders it possible to identify and control the operation of the light radiation source, preventing an improper operation thereof.

According to the invention, a light radiation source suitable for cooperating with an identification system according to claim 1 comprises an identification circuit arranged to communicate with the control circuit via at least a portion of the first electric wire. The identification circuit may be used to store, for example, information on the manufacturer of the lamp, the type of lamp, and/or its wattage.

An embodiment of the light radiation source according to the invention is characterized in that the identification circuit is magnetically coupled to the first electric wire via a current transformer. A magnetic coupling between the electric wire and the identification circuit removes the need to modify the current-supply wiring and the electrical contacts. The magnetic coupling provides a read-out of the identification circuit via a modulated antenna current signal.

An embodiment of the light radiation source according to the invention is characterized in that the current transformer comprises a magnetic core surrounding the first electric wire and a coil wound around the magnetic core, which coil is coupled to the identification circuit, providing a relatively simple manner of magnetic coupling.

An embodiment of the light radiation source according to the invention is characterized in that the identification circuit is coupled via a first output to the first electric wire and via a second output to a conducting element of the light radiation source. This embodiment renders it possible to feed the voltage induced in the first electric wire to the identification circuit and to read the data from the identification circuit through measuring of the modulated antenna voltage signal.

An embodiment of the light radiation source according to the invention is characterized in that the light radiation source is a mercury vapor discharge lamp for generating UV radiation for suntanning purposes or for disinfection purposes. Identification of these lamps can prevent physical injury caused by the use of an incorrect type of lamp and can prevent an insufficient degree of disinfection.

According to the invention, a solarium comprises an identification system for a light radiation source according to claim 1.

An embodiment of the solarium according to the invention is characterized in that, during operation, the first transmitting antenna operates against a reference potential created by a conducting metal part of the solarium. As a result, the antenna signal is generated with respect to the metal part. At least a portion of the internal wiring of the solarium acts as the first transmitting antenna.

According to the invention, a UV disinfection system comprises an identification system for a light radiation source according to claim 1.

DESCRIPTION OF EMBODIMENTS

Figure 1:
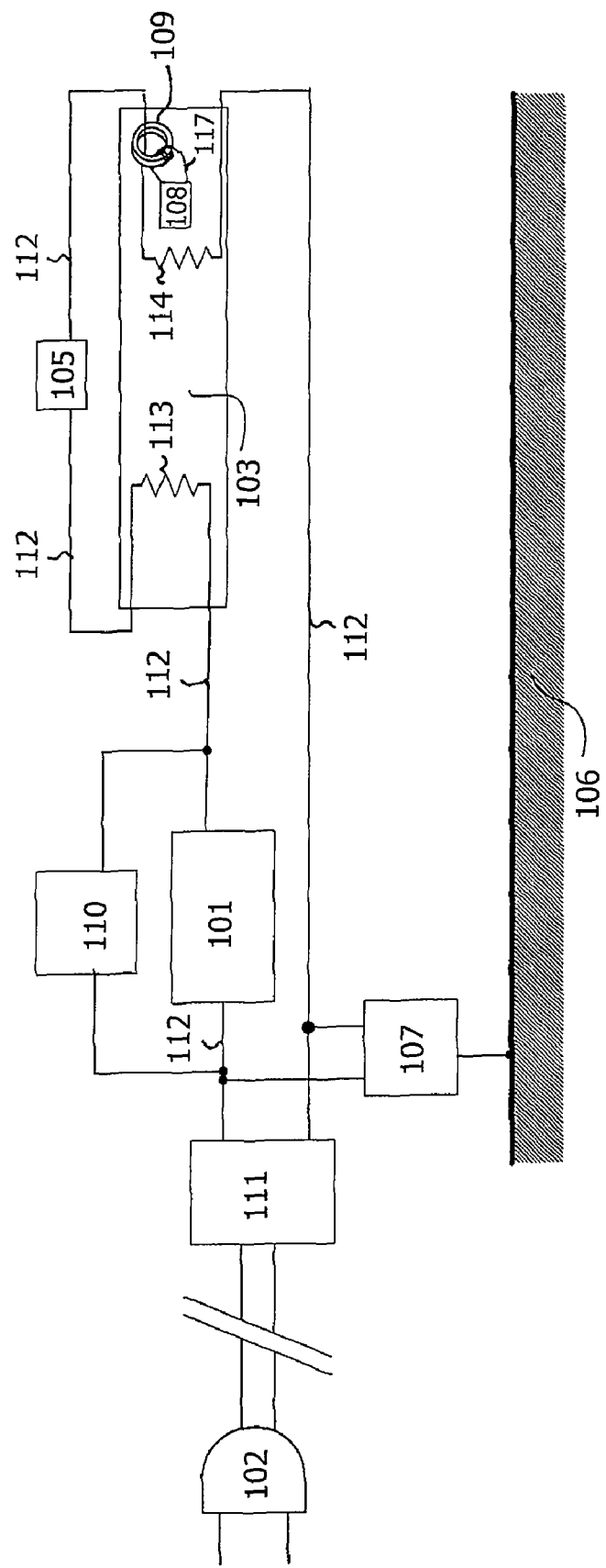
FIG. 1 schematically shows a mercury vapor discharge lamp having an identification circuit and an identification system according to the invention.

FIG. 1 schematically shows a mercury vapor discharge lamp 103 having an identification circuit 108, and an identification system having a controller 107. The lamp 103 is connected to the power grid via connector 102, and the lamp is powered via ballast circuit 101. The ballast circuit 101 may be an electronic ballast or an electromagnetic ballast. The ballast circuit 101 is coupled in series with the electric wire 112 in one direction. The lamp 103 is, for example, a UV radiation source in a solarium, a disinfection installation lamp, or a device for medical treatment, or alternatively a visible light radiation source for general illumination purposes, or for liquid crystal display backlighting applications. In an alternative embodiment, the controller 107 is integrated into the ballast circuit 101. The ballast circuit 101 and the controller 107 are connected to the lamp 103 via an electric wire 112. The electric wire may comprise sockets, not shown in FIG. 1, as well as electrical contacts of the lamp 103, not shown in FIG. 1, that are inserted into the sockets. The lamp 103 comprises two electrodes 113 and 114, coupled to the electric wire 112. A starter 105 is coupled in series with the first and the second electrode 113 and 114, via electric wire 112. The identification circuit 108 is integrated into the lamp 103. The identification circuit is an integrated circuit having a digital memory for storage of information that can be used for identification of the lamp, for example in the form of a radio frequency identification chip. The information may be related to the type of the lamp, the manufacturer, a serial number, the wattage, the lumen output, to name a few, or a combination thereof. The identification circuit 108 operates at a frequency of 13.56 MHz, in accordance with the ISO-15693 or ISO-18000 standard of the International Organization for Standardization. In other embodiments, however, the identification circuit 108 may operate at a different frequency. The identification circuit 108 is magnetically coupled to the electric wire 112 via a current transformer, comprising a magnetic core 109 through which the electric wire 112 is passed and around which a coil 117 is wound. The coil 117 is connected to identification circuit 108. The controller 107 is coupled to a conducting ground 106 providing a reference potential and to the electric wire 112. In the case of a solarium, the conducting ground 106 is the metal housing of a solarium that is usually, but not necessarily, connected to ground. The first electric wire 112 is capacitively coupled to the conducting ground 106. In operation, prior to activating the ballast circuit 101 for powering the electrodes 113 and 114, the information stored in the memory of the identification circuit 108 is read by the controller 107 via a portion of the electric wire 112, i.e. that part of the electric wire 112 that goes through the magnetic core 109, that acts as an antenna. The controller 107 applies a voltage to the electric wire 112, which induces an antenna current signal in the electric wire 112 due to the capacitive coupling of the electric wire 112 with the conducting ground 106. The magnetic core 109 senses the antenna current signal and generates an electric field, which generates an electric current through coil 117, activating and energizing the identification circuit 108. The identification circuit 108 modulates the antenna current signal, and this modulated antenna current signal is communicated to the controller 107 via the electric wire 112, allowing the controller 107 to read data from the identification circuit 108. The antenna current signal is bypassed across the ballast circuit 101 via bypass circuit 110, for example in the form of a capacitor, that is coupled to the electric wire 112 in parallel with the ballast circuit 101, since the ballast circuit 101 acts as a blocker for the high-frequency antenna current signal. A signal blocker 111, for example in the form of an inductor, prevents coupling of the antenna current signal to the outside world. The information read from the identification circuit 108 by controller 107 is compared by the controller 107 with reference data. For example, information related to the type of lamp read from the identification circuit 108 is compared with reference data on the type or types of lamps that are allowable for the particular purpose. This reference data is stored in a memory, not shown in FIG. 1, of the controller 107. If the lamp 103 is identified as allowable, the controller 107 generates a signal in order to activate the ballast circuit 101 for powering the lamp 103. A heating voltage is applied to the electrodes 113 and 114 via electric wire 112. After a gas discharge has been initiated in the lamp 103, the lamp 103 is powered normally to maintain this gas discharge in the lamp 103. If the lamp 103 is identified as not allowable, however, the controller 107 does not generate a signal to activate the ballast circuit 101 for powering the lamp 103. The controller may also generate a signal to warn the user that the lamp 103 should be replaced by a correct type of lamp. An advantage of this embodiment, wherein a portion of the first electric wire 112 is used as an antenna, over the use of the first electric wire 112 as a current loop for reading the identification circuit 108 is that the use of the latter, prior art identification system in a grounded metal device, such as a solarium, is limited to devices with a relatively small length of the first electric wire 112 because of the considerable amount of parasitic capacitances and inductances that are present.

Figure 2:
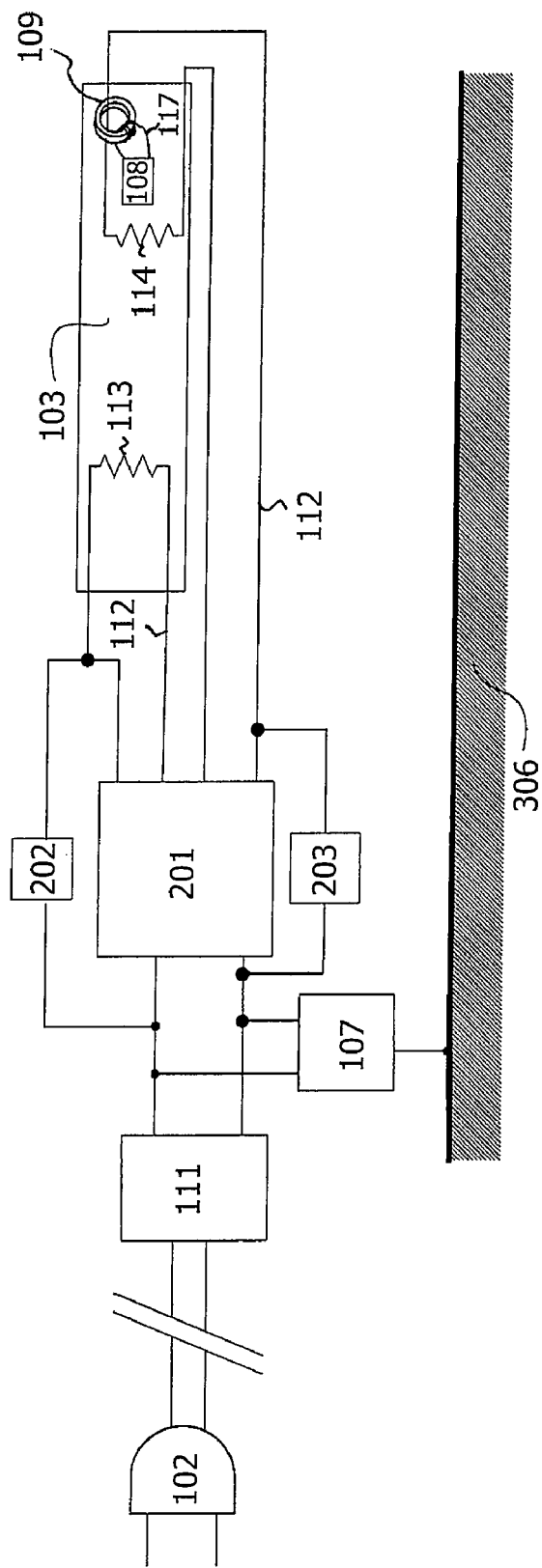
FIG. 2 schematically shows a mercury vapor discharge lamp having an identification circuit and an alternative identification system according to the invention.

Referring to FIG. 2 now, showing an alternative embodiment, the identification system comprises an electronic ballast circuit 201 coupled in series with the electric wire 112 in both directions. Two bypass circuits 202 and 203 are placed in parallel to the ballast circuit 201, in both directions of the electric wire 112, for bypassing the antenna current signal across the ballast circuit 201. In operation, the information stored in the memory of the identification circuit 108 is read by a controller 107 via the electric wire 112 that acts as an antenna in an identical manner as described for the embodiment shown in FIG. 1, before the ballast circuit 201 for powering the electrodes 113 and 114 is activated. If the lamp 103 is identified as allowable, the controller 107 will generate a signal in order to activate the ballast circuit 201 for powering the lamp 103. If the lamp 103 is identified as not allowable, the controller 107 will not generate such a signal. The controller 107 may generate a signal to warn the user that the lamp 103 should be replaced by a correct type of lamp.

Figure 3:
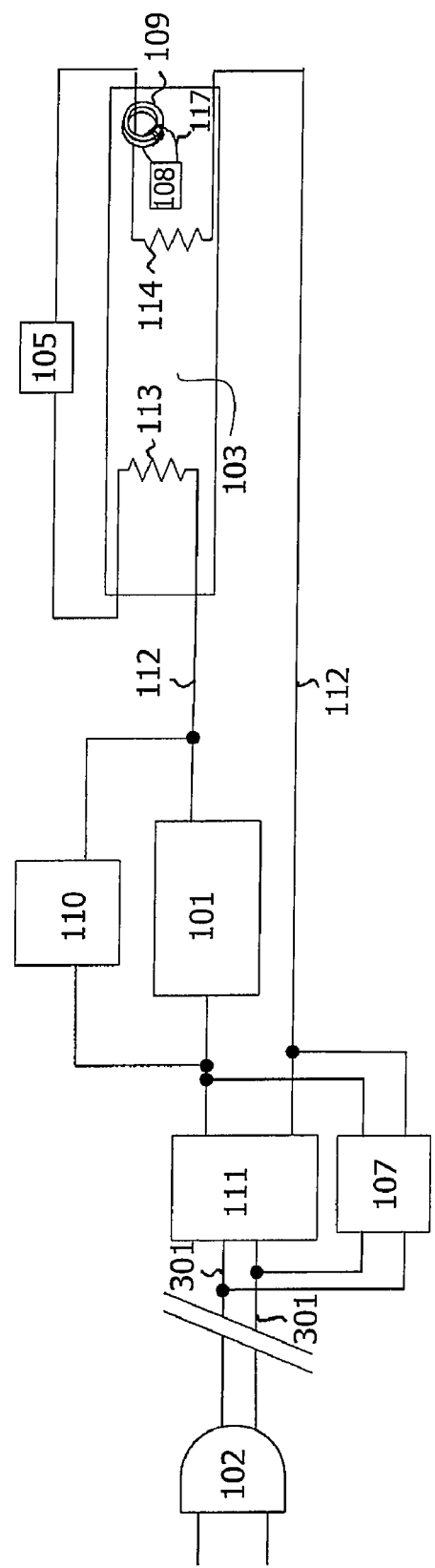
FIG. 3 schematically shows a mercury vapor discharge lamp having an identification circuit and a further alternative identification system according to the invention.

Referring to FIG. 3, in a further alternative embodiment, the controller 107 is coupled to the electric wire 112 in both directions in parallel to the signal blocker 111, as well as to the electric wire 301 in both directions. The electric wire 112 acts as a first antenna, and the electric wire 301 acts as a second antenna. In operation, the information stored in the memory of the identification circuit 108 is read by the controller 107, using a portion of the electric wire 112, before the ballast circuit 101 for powering the electrodes 113 and 114 is activated. The controller 107 applies a voltage to both the electric wire 112 and the electric wire 301, such that the electric wire 112 and the electric wire 301 behave as a dipole antenna. As a result, an antenna current signal is generated in the electric wire 112. Magnetic core 109 senses the antenna current signal and generates an electric field, which generates an electric current through coil 117, activating and energizing the identification circuit 108. The identification circuit 108 modulates the antenna current signal, and this modulated antenna current signal is communicated to the controller 107 via the electric wire 112, allowing the controller 107 to read data from the identification circuit 108. The antenna current signal is bypassed across the ballast circuit 101 via bypass circuit 110 that is coupled to the electric wire 112 in parallel to the ballast circuit 101, since the ballast circuit 101 acts as a blocker to the high-frequency antenna current signal. A signal blocker 111, for example in the form of an inductor, prevents a coupling of the antenna current signal to the electric wire 301. The information read from the identification circuit 108 by controller 107 is compared with reference data. For example, information related to the type of the lamp read from the identification circuit 108 is compared with reference data on the type or types of lamps that are allowable for the particular purpose. This reference data is stored in a memory, not shown in FIG. 3, of the controller 107. If the lamp 103 is identified as allowable, a controller 107 will generate a signal in order to activate the ballast circuit 101 for powering the lamp 103. A heating voltage is applied to the electrodes 113 and 114 via electric wire 112. After a gas discharge has been initiated in the lamp 103, the lamp 103 is powered normally to maintain a gas discharge in the lamp 103. If the lamp 103 is identified as not allowable, the controller 107 will not generate a signal to activate the ballast circuit 101 for powering the lamp 103. The controller 107 may generate a signal to warn the user that the lamp 103 should be replaced by a correct type of lamp.

In an alternative embodiment, the controller 107 keeps track of the time during which the lamp 103 is energized by the ballast circuit 101 and stores this information at regular time intervals in the memory of the identification circuit 108, for example in the form of the number of hours that the lamp has been in operation. Prior to activating the lamp 103 again, the number of operating hours as well as a reference value are read by the controller 107 from the identification circuit 108, and these values are compared by the controller 107. Alternatively, the number of operating hours and/or the reference value is stored in a memory of the controller 107 itself. If the number of operating hours exceeds the relevant reference value, the controller 107 will prevent operation of the lamp 103. As the efficiency of a lamp decreases over time, and this decrease is generally fairly constant over time, it can be prevented in this way that the efficiency of the lamp will be too low for a given application. In a further alternative embodiment, the controller 107 keeps track of the number of start-ups of the lamp 103 and stores this information in the identification circuit 108. Prior to activating the lamp 103, the number of start-ups is read by the controller 107 from the identification circuit 108 and compared with a reference value. If the number of start-ups exceeds the reference value, the controller 107 will prevent operation of the lamp 103. Alternatively, both the number of operating hours and number of start-ups may be recorded by the controller 107 and stored in the identification circuit 108 or a memory of the controller itself, and operation of the lamp 103 is prevented if one of these parameters exceeds a reference value.

In a further alternative embodiment, the controller 107 stores information on the operating time of the lamp in the identification circuit 108 at regular time intervals and uses this information together with known information on the decrease of the efficiency of the lamp 103 over time to calculate an adapted voltage and/or current intensity for the lamp 103, such that the lumen output of the lamp 103 remains fairly constant over time. The controller 107 sends the adapted value of the voltage and/or current intensity to the ballast circuit 101, which applies the new value(s) to the lamp 103 via the electric wires 112. Information on the decrease of the lamp efficiency over time may be stored in the identification circuit 108 and read by the controller 107, or it is stored in a memory of the controller 107 itself.

Figure 4:
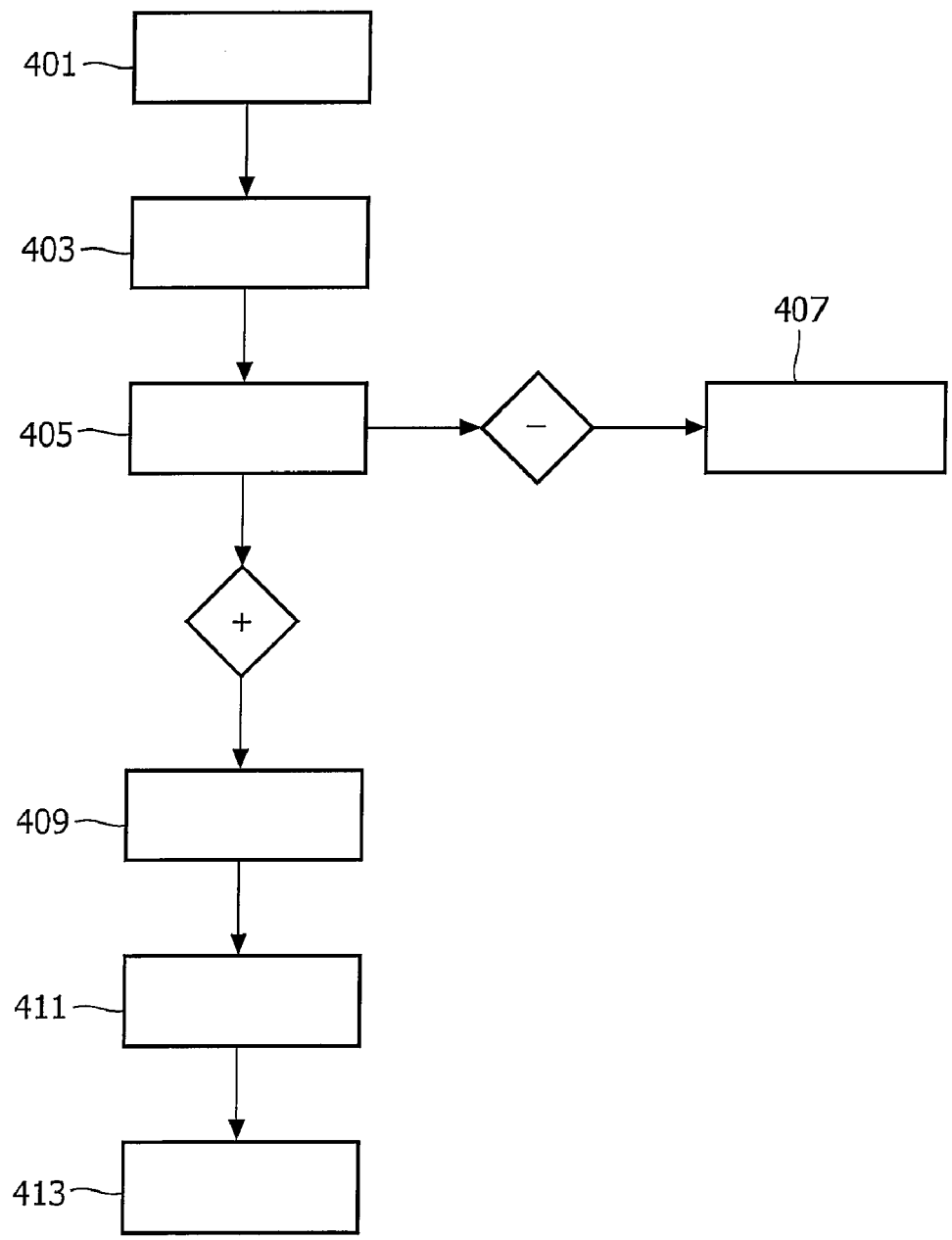
FIG. 4 is a flowchart of a method of operating a mercury vapor discharge lamp according to the invention, using an identification system as shown in FIG. 1.

FIG. 4 is a flowchart of a method of operating a low-pressure mercury vapor discharge lamp, using an identification system as shown in FIG. 1. In a first step 401, a controller 107 is activated without energizing the lamp 103 through switching-on of the main current supply of the identification system. In step 403, controller 107 is activated to apply a voltage to the electric wire 112, and data are read from the identification circuit 108, for example on the serial number of the lamp 103. In step 405, the controller 107 compares the read data with reference data, and if the result of the comparison is negative, operation of the lamp is prevented in step 407 in that the ballast circuit 101 is not activated to energize the lamp 103. In an alternative embodiment, the control signal may also generate a signal to notify the user of the negative result of the comparison. If the result of the comparison is positive, the controller 107 generates a signal in step 409 in order to authorize the ballast circuit 101 to energize the lamp 103. In step 411, a heating voltage is applied to the electrodes 113 and 114. After a gas discharge has been initiated in the lamp 103, the lamp 103 is powered in step 413 in a normal way to maintain a gas discharge in the lamp.

In an alternative embodiment, the controller 107 keeps tracks of the operating time of the lamp 103, for example in the form of the number of operating hours. The number of operating hours is stored in the identification circuit 108. The controller 107 updates the number of operating hours in an additional step, not shown in FIG. 4, at regular time intervals, for example every hour. If the number of operating hours exceeds a reference value, the controller 107 activates the ballast circuit 101 in a further additional step, not shown in FIG. 4, to interrupt the operation of the lamp 103 by switching off the power supply to the lamp.

In another alternative embodiment, the controller 107 alters the operation of the lamp 103 in another further additional step, not shown in FIG. 4, by determining a value of the voltage and/or current intensity such that the lumen output of the lamp 103 remains fairly constant, taking into account the number of operating hours of the lamp 103 and the decrease in efficiency of the lamp over time. The controller 107 sends the adapted value of the voltage and/or current intensity to the ballast circuit 101, which applies the new value(s) to the lamp 103.

Figure 5:
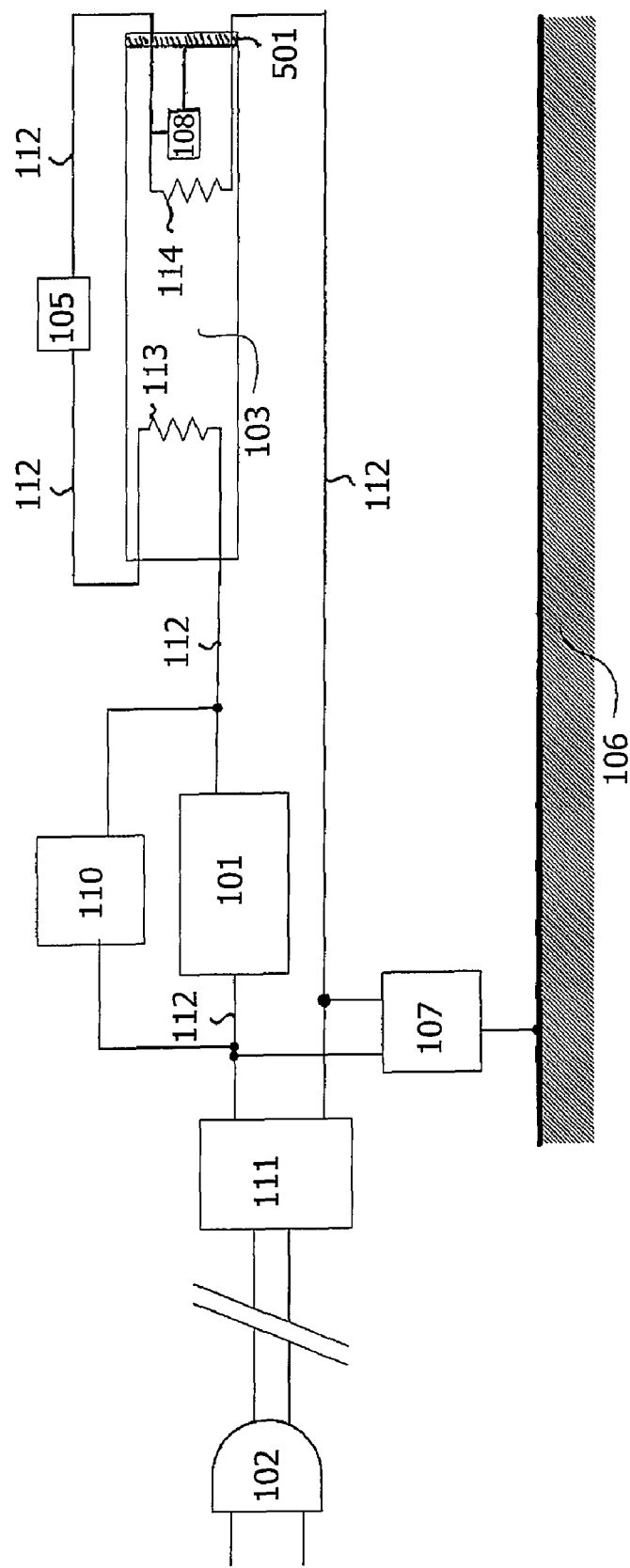
FIG. 5 schematically shows an alternative mercury vapor discharge lamp having an identification circuit and an identification system according to the invention.

FIG. 5 shows an alternative embodiment of a mercury vapor discharge lamp 103 and an identification system. The identification circuit 108 is connected via a positive output to the electric wire 112 and via a negative output to the lamp cap 501. In an alternative embodiment, the negative output is coupled to a different conducting part of the lamp 103. The lamp cap 501 provides a sufficiently large reference ground for the identification circuit 108 to guarantee a sufficient capacitive coupling with the conductive ground 106. In operation, the controller 107 applies a voltage to the electric wire 112. The capacitive coupling of the identification circuit 108 with the ground 106 creates a voltage difference. The voltage induced in the electric wire 112 is fed to the identification circuit 108. The identification circuit 108 modulates the antenna voltage signal, and this modulated antenna voltage signal is communicated to the controller 107 via the electric wire 112, allowing the controller 107 to read data from the identification circuit 108. This data is compared with reference data, and if the lamp 103 is allowable, a signal is generated to activate the ballast circuit 101 to start operation of the lamp 103, otherwise operation of the lamp 103 is prevented.

Figure 6:
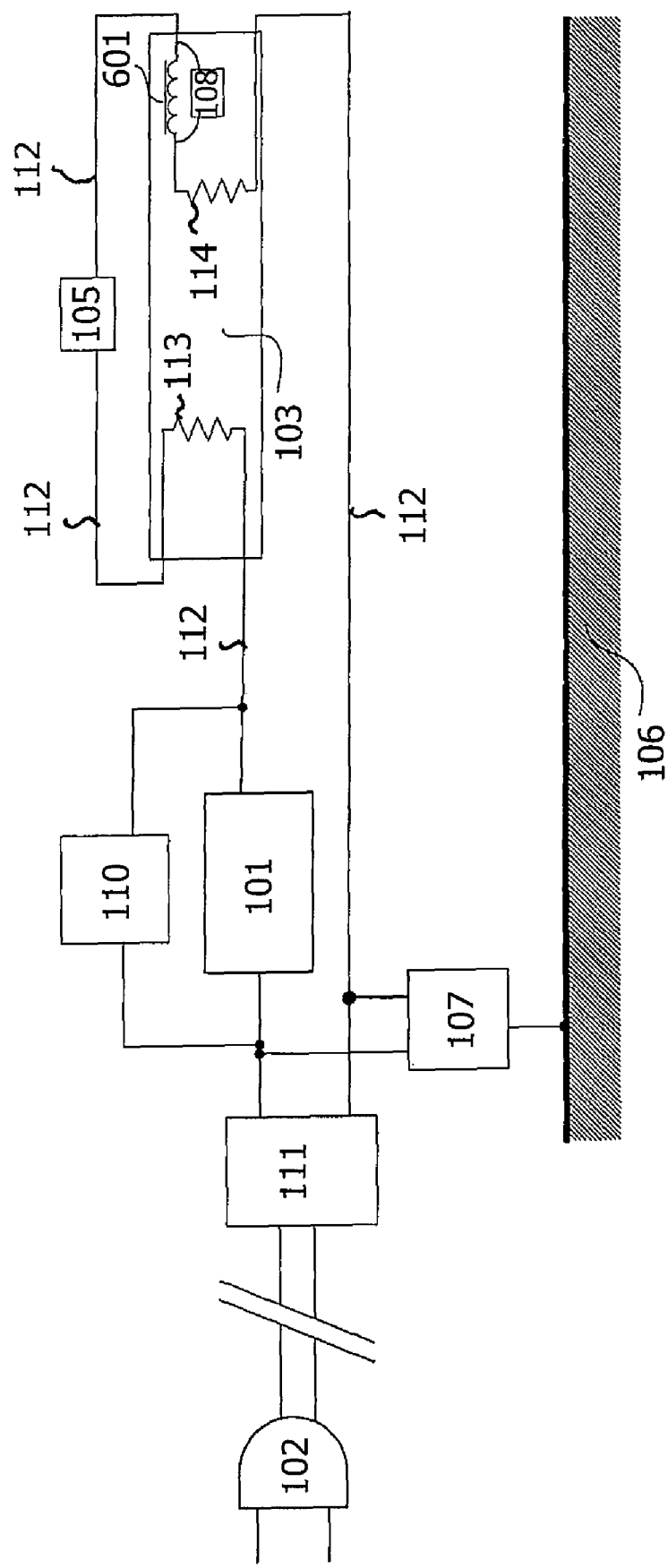
FIG. 6 schematically shows a further alternative mercury vapor discharge lamp having an identification circuit and an identification system according to the invention.

FIG. 6 shows a further alternative embodiment of a mercury vapor discharge lamp 103 and an identification system. The lamp 103 has an identification circuit 108 that is coupled via both of its outputs to the electric wire 112. Parallel to the identification circuit 108, a coil 601 is coupled to the electric wire 112. In operation, the controller 107 applies a voltage to the electric wire 112, which induces an antenna current signal in the electric wire 112 owing to the capacitive coupling of the electric wire 112 with the conducting ground 106. The coil 601 blocks the antenna current signal, and the antenna current flows through the identification circuit 108. The identification circuit 108 modulates the antenna current signal, and this modulated antenna current signal is communicated to the controller 107 via the electric wire 112, allowing the controller 107 to read data from the identification circuit 108. This data is compared with reference data, and if the lamp 103 is allowable, a signal is generated to activate the ballast circuit 101 to start operation of the lamp 103, otherwise operation of the lamp 103 is prevented. The current for energizing the lamps flows through the coil 601 during normal operation of the lamp 103.

In an alternative embodiment, the lamp 103 is an incandescent lamp, for example for general illumination purposes, or an infrared lamp for medical treatment. In general, an incandescent lamp has only one electrode, and the identification circuit 108 can be integrated in the incandescent lamp as shown in FIG. 1 for electrode 114.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An identification system for a light radiation source, comprising a control circuit for energizing the light radiation source and for communicating with an identification circuit, wherein the identification circuit is integrated into the light radiation source and is arranged for storing data relating to the light radiation source, and wherein, during operation, the control circuit is electrically coupled to the light radiation source via a first electric wire of the control circuit provided for energizing the light radiation source, and wherein a part of the first electric wire that is integrated into the light radiation source has a capacitive coupling with the identification circuit and acts as a first transmitting antenna for providing communication between the control circuit and the identification circuit.

2. An identification system for a light radiation source according to claim 1, wherein the identification system is further arranged for controlling the operation of the light radiation source in dependence on data retrieved from the identification circuit.

3. An identification system for a light radiation source according to claim 1, wherein the identification system is further arranged to store information on or corresponding to the number of operating hours of the light radiation source.

4. An identification system for a light radiation source according to claim 3, wherein the identification system is further arranged to generate a signal to alter the energizing of the light radiation source in dependence on the number of operating hours in order to maintain a substantially constant radiation output.

5. An identification system for a light radiation source according to claim 1, wherein the identification system is further arranged to store information on or corresponding to the number of start-ups of the light radiation source.

6. An identification system for a light radiation source according to claim 1, wherein the control circuit is further arranged to communicate with the identification circuit by means of a modulated antenna current signal.

7. An identification system for a light radiation source according to claim 6, wherein the control circuit is coupled to a conducting ground.

8. An identification system for a light radiation source according to claim 7, further comprising:
an electromagnetic ballast for energizing the light radiation source via the first electric wire,
a signal-passing device coupled to the first electric wire in parallel to the electromagnetic ballast for passing a modulated antenna current signal or a modulated antenna voltage signal used for communication between the control circuit and the identification circuit.

9. An identification system for a light radiation source according to claim 8 further comprising:
a signal-blocking device, coupled in series with the electromagnetic ballast, wherein the ballast prevents the modulated antenna current signal or the modulated antenna voltage signal used for communicating with the identification circuit from proceeding in the direction of a power supply provided for energizing the electromagnetic ballast.

10. An identification system for a light radiation source according to claim 6, wherein the control circuit is further electrically coupled to a second electric wire provided for energizing the light radiation source, such that, during operation, the second electric wire acts as a second transmitting antenna cooperating with the first transmitting antenna as a dipole antenna.

11. An identification system for a light radiation source according to claim 1, wherein the control circuit is further arranged to communicate with the identification circuit by means of a modulated antenna voltage signal.

12. A method for operating an identification system for a light radiation source according to claim 1, the method comprising the following steps:
reading-out of data stored in the identification circuit,
comparing the read-out data with reference data,
authorizing, preventing, interrupting or altering the operation of the light radiation source.

13. A light radiation source for cooperating with an identification system according to claim 1, comprising an identification circuit arranged to communicate with the control circuit via at least a portion of the first electric wire.

14. A light radiation source according to claim 13, wherein the identification circuit is magnetically coupled to the first electric wire via a current transformer.

15. A light radiation source according to claim 14, wherein the current transformer comprises a magnetic core surrounding the first electric wire and a coil wound around the magnetic core, said coil being coupled to the identification circuit.

16. A light radiation source according to claim 13, wherein the identification circuit is coupled via a first output to the first electric wire and via a second output to a conducting element of the light radiation source.

17. A light radiation source according to claim 13, wherein the light radiation source is a mercury vapor discharge lamp for generating UV radiation for suntanning purposes or for disinfection purposes.

18. A solarium comprising an identification system for a light radiation source according to claim 1.

19. A solarium according to claim 18, wherein, during operation, the first transmitting antenna operates against a reference potential created by a metal part of the solarium.

20. A UV disinfection system comprising an identification system for a light radiation source according to claim 1.

* * * * *